(12) United States Patent
Gaffney et al.

(10) Patent No.: US 7,795,469 B2
(45) Date of Patent: Sep. 14, 2010

(54) PROCESS FOR THE SELECTIVE (AMM) OXIDATION OF LOWER MOLECULAR WEIGHT ALKANES AND ALKENES

(75) Inventors: Anne Mae Gaffney, West Chester, PA (US); Scott Han, Lawrenceville, NJ (US)

(73) Assignee: Rohm and Haas Company, Philadelphia, PA (US)

(*) Notice: Subject to any disclaimer, the term of this patent is extended or adjusted under 35 U.S.C. 154(b) by 159 days.

(21) Appl. No.: 11/985,671

(22) Filed: Nov. 16, 2007

(65) Prior Publication Data

US 2008/0154056 A1 Jun. 26, 2008

Related U.S. Application Data

(60) Provisional application No. 60/876,304, filed on Dec. 21, 2006.

(51) Int. Cl.
*C07C 51/16* (2006.01)
(52) U.S. Cl. .................................................. 562/545
(58) Field of Classification Search ............... 558/319; 562/545
See application file for complete search history.

(56) References Cited

U.S. PATENT DOCUMENTS

| | | | |
|---|---|---|---|
| 5,281,745 A * | 1/1994 | Ushikubo et al. ........... 558/319 |
| 5,380,933 A | 1/1995 | Ushikubo et al. |
| 6,043,185 A | 3/2000 | Cirjak et al. |
| 6,383,978 B1 | 5/2002 | Bogan, Jr. |
| 6,403,525 B1 | 6/2002 | Chaturvedi et al. |
| 6,407,031 B1 | 6/2002 | Chaturvedi et al. |
| 6,407,280 B1 | 6/2002 | Chaturvedi et al. |
| 6,461,996 B2 | 10/2002 | Chaturvedi et al. |
| 6,472,552 B1 | 10/2002 | Bogan, Jr. |
| 6,504,053 B1 | 1/2003 | Chaturvedi et al. |
| 6,589,907 B2 | 7/2003 | Chaturvedi et al. |
| 6,624,111 B2 | 9/2003 | Chaturvedi et al. |
| 6,777,571 B2 * | 8/2004 | Chaturvedi et al. ......... 558/323 |
| 6,914,150 B2 * | 7/2005 | Gaffney et al. .............. 558/319 |
| 7,288,669 B2 * | 10/2007 | Gaffney et al. .............. 558/320 |
| 2005/0137415 A1 | 6/2005 | Bogan, Jr. et al. |

FOREIGN PATENT DOCUMENTS

EP 1 577 406 A 7/2005

* cited by examiner

*Primary Examiner*—Rei-tsang Shiao
(74) *Attorney, Agent, or Firm*—Marcella M. Bodner

(57) ABSTRACT

An improved process for the production of unsaturated carboxylic acids and unsaturated nitriles from their corresponding $C_3$ to $C_5$ alkanes, or mixtures of $C_3$ to $C_5$ alkanes and alkenes, that involves oxidation in the presence of a supported Mo—V-based mixed metal oxide catalyst in a multi-stage reaction system which employs both separation of the oxidation product from one or more intermediate effluent streams, as well as feeding additional oxygen to reaction zones subsequent to the first reaction zone.

10 Claims, 2 Drawing Sheets

PROCESS FOR THE SELECTIVE (AMM) OXIDATION OF LOWER MOLECULAR WEIGHT ALKANES AND ALKENES

CROSS REFERENCE TO RELATED PATENT APPLICATIONS

This is a non-provisional patent application of U.S. provisional patent application Ser. No. 60/876,304 filed Dec. 21, 2006.

FIELD OF THE INVENTION

The present invention relates to improved processes for the selective oxidation of $C_3$ to $C_5$ alkanes and alkenes, including propane and isobutane, and mixtures thereof, to their corresponding unsaturated carboxylic acids and unsaturated nitriles, including acrylic acid, methacrylic acid, acrylonitrile and methacrylonitrile.

BACKGROUND OF THE INVENTION

Unsaturated carboxylic acids, such as acrylic acid and methacrylic acid, are industrially important as starting materials for various synthetic resins, coating materials and plasticizers. Two-step vapor phase reaction processes from alkenes have historically been practiced for the production of unsaturated carboxylic acids, including acrylic acid and methacrylic acid, and these processes are still widely used today. However, in view of the price difference between alkanes and their corresponding alkenes (for example, propane versus propene, and isobutane versus isobutene), processes involving single-step vapor phase catalytic oxidation of alkanes, alkenes, and mixtures thereof, to produce unsaturated carboxylic acids have been developed with varying degrees of success. Generally, such methods involve subjecting an alkane, an alkene, or a mixture thereof, to a vapor phase catalytic oxidation reaction in the presence of a suitable mixed metal oxide catalyst, to produce the corresponding unsaturated carboxylic acid.

Unsaturated nitriles, such as acrylonitrile and methacrylonitrile, have been industrially produced as important intermediates for the preparation of fibers, synthetic resins, synthetic rubbers, and the like. A currently popular method for producing such nitriles is to subject an olefin, such as propene, to a vapor phase catalytic reaction with ammonia, in the presence of a suitable catalyst, at a high temperature. Again, in view of the price difference between alkanes and their corresponding alkenes, efforts have been made to develop methods and catalysts for producing acrylonitrile or methacrylonitrile from feedstocks comprising a lower alkane, such as propane or isobutane, which is reacted with ammonia in a gaseous phase, in the presence of a suitable mixed metal oxide catalyst.

For example, U.S. Patent Application Publication No. US2005/0137415 discloses a single-step vapor phase catalytic oxidation process which involves interstage condensation of a desired product from one or more product streams intermediate adjacent reaction zones arranged in series, as well as staged addition of supplemental oxygen to one or more reaction zones downstream of the first reaction zone. More particularly, the process disclosed in US 2005/0137415 is performed using a reaction system having at least two reaction zones arranged in series with one another, wherein alkanes, alkenes, and mixtures thereof, are converted to their corresponding unsaturated carboxylic acids or unsaturated nitriles in each of the reaction zones, in the presence of at least one suitable catalyst, and at least a portion of the intermediate product stream of each reaction zone is fed to the subsequent downstream reaction zone, until the final reaction zone is reached.

In the process disclosed in U.S. Patent Application Publication No. US2005/0137415, less than the full stoichiometrically required amount of oxygen is fed to the first reaction zone with the reactants, and at a least a portion of the desired product is separated (e.g., by condensation) from the intermediate product stream of at least one reaction zone, while the remaining portion of the intermediate product stream is fed to the subsequent downstream reaction zone, along with supplemental oxygen. Unexpected increases in the overall yield of desired product were achieved. The overall yield of this process unexpectedly exceeded the cumulative sum of the independent yields of each of the reaction zones.

Catalyst formulations suitable for use in the aforesaid oxidation process are proprietary to the catalyst suppliers, but the technology is well-established and such catalysts are commercially available from various sources. Various suitable catalysts, and methods of making same, are disclosed and fully described in U.S. Pat. Nos. 5,380,933, 6,383,978, 6,403,525, 6,407,031, 6,407,280, 6,461,996, 6,472,552, 6,504,053, 6,589,907 and 6,624,111. Based on recent research, it appears that catalyst formulations which contain a mixed metal oxide comprising, as essential components, molybdenum (Mo) and vanadium (V) are particularly suitable for use in commercial processes for single-step vapor phase catalytic oxidation of alkanes, alkenes, and mixtures thereof to their corresponding unsaturated carboxylic acids and unsaturated nitriles.

For example, U.S. Pat. No. 5,380,933 discloses a catalyst useful for producing an unsaturated carboxylic acid from an alkane by single-step vapor phase catalytic oxidation, where the catalyst contains a mixed metal oxide comprising, as essential components, Mo, V, Te, X and oxygen (O), wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: $0.25 < r(Mo) < 0.98$, $0.003 < r(V) < 0.5$, $0.003 < r(Te) < 0.5$ and $0.003 < r(X) < 0.5$, wherein $r(Mo)$, $r(V)$, $r(Te)$ and $r(X)$ are the molar fractions of Mo, V, Te and X, respectively, based on the total amount of the essential components exclusive of oxygen. (supported?)

Similarly, U.S. Patent Application Publication No. 2005/0239643 discloses structured catalysts suitable for conversion of alkanes, alkenes, and mixtures thereof to their corresponding unsaturated carboxylic acids. These catalysts comprise one or more mixed metal oxides, each of which satisfies the expression:

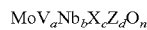

$$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Si, Pb, P, Bi, Y, Ce, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements. The aforesaid mixed metal oxide is in contact with and supported on a three dimensional form of continuous unitary structures having openings that facilitate movement of gas phase reactants and products and the three dimensional form comprises ceramic foams and ceramic monoliths selected from the group consisting of: cordierite, alumina, zirconia, silica, aluminosilicate zeolites, phosphosilicate zeolites, other zeolites and combinations thereof. The one or more mixed metal oxide catalysts are deposited on the ceramic foams and ceramic monoliths by methods selected from the group consisting of impregnation, wash coating, slurry dip-coating, chemical vapor deposition, physical vapor deposition, precipitation and combinations thereof.

U.S. Pat. No. 5,281,745 discloses a method for producing an unsaturated nitrile comprising subjecting an alkane and ammonia in the gaseous state to catalytic oxidation in the presence of a catalyst comprising a mixed metal oxide catalyst represented by the empirical formula:

$$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and wherein the catalyst has X-ray diffraction peaks at the following angles (±0.3°) of 2θ in its X-ray diffraction pattern: 22.1°, 28.2°, 36.2°, 45.2° and 50.0°. The ammoxidation catalyst of U.S. Pat. No. 5,281,745 may be used together with a conventional carrier such as silica, alumina, titania, alumnosilicate or diatomaceous earth.

In addition, a promoted ammoxidation catalyst suitable for converting alkanes to unsaturated nitriles is disclosed in U.S. Pat. No. 6,043,186 and has the formula $$Mo_{1.0}V_aNb_bX_cZ_eO_n$$

where X is at least one element selected from the group consisting of tellurium and antimony; Z is at least one element selected from the group consisting of ytterbium, dysprosium and erbium; E is at least one element selected from the group consisting of neodymium, samarium, lanthanum, praseodymium, europium, gadolinium, terbium, holmium, thulium, lutetium and scandium; and a, b, c, d, e, and n are, respectively, the atomic ratios of vanadium, niobium, X, Z, E and oxygen, relative to molybdenum, wherein: 0.1≦a≦1.0, 0.01≦b≦1.0, 0.01≦c≦1.0, 0≦d≦0.1, 0≦e≦0.1, 0.001≦d+e≦0.1, and n is a number determined by and consistent with the valence requirements of the other elements present in the catalyst. The catalyst may be supported on a silica carrier.

U.S. Pat. No. 6,043,185 also discloses a catalyst useful in the manufacture of acrylonitrile or methacrylonitrile by vapor phase catalytic reaction of a paraffin, selected from propane and isobutene, with molecular oxygen and ammonia, by contact of the reactants in a reaction zone with a catalyst having the empirical formula:

$$Mo_aV_bSb_cGa_dX_eO_x$$

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present.

It is generally understood in the field of catalysis that increasing the surface area of a solid phase catalyst, such as by loading or depositing it onto a support material, may increase product yield, and that suitable supports vary depending on the nature of the starting materials and operating conditions to which the catalyst will be exposed. It is also known that reduction of the mass quantity of catalyst disposed in a particular reaction zone generally results in a proportional decrease in desired product yield.

The present invention provides a process for preparation of unsaturated carboxylic acids or unsaturated nitriles from their corresponding alkanes, alkenes, and mixtures thereof, in the presence of a supported mixed metal oxide catalyst. The process of the present invention, delivers unexpected increases in selectivity and yield which exceed the expected sum of selectivities and yields of the combined features.

SUMMARY OF THE INVENTION

The present invention provides a process for producing unsaturated carboxylic acids or unsaturated nitriles by vapor phase oxidation reaction of their corresponding $C_3$ to $C_5$ alkanes, $C_3$ to $C_5$ alkenes, and mixtures thereof, using a reaction system having at least two reaction zones arranged in series with one another and at least one catalyst capable of catalyzing the vapor phase oxidation reaction disposed in each of the at least two reaction zones, wherein at least one intermediate effluent stream exits a preceding one of the at least two reaction zones and is at least partially fed to a subsequent one of the at least two reaction zones. The process comprises the steps of: separating the at least one intermediate effluent stream into at least an intermediate product stream comprising an oxidation product selected from the group consisting of an unsaturated carboxylic acid and an unsaturated nitrile, and an intermediate feed stream comprising starting materials selected from the group consisting of an unreacted $C_3$ to $C_5$ alkane, an unreacted $C_3$ to $C_5$ alkene, and mixtures thereof; feeding the intermediate feed stream to the subsequent reaction zone; and feeding an oxygen-containing gas to the subsequent reaction zone.

The catalyst disposed in each of the at least two reaction zones comprises a three dimensional support and a mixed metal oxide having the empirical formula:

$$Mo_aV_bN_cX_dO_e$$

wherein N is at least one element selected from the group consisting of Te and Se; X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein a, b, c, d and e are, respectively, the atomic ratios of molybdenum, vanadium, N, X and oxygen, and when a=1, b=0.01 to 1.0, c=0.01 to 1.0, d=0.01 to 1.0, and e is dependent on the oxidation state of the other elements. The element N of the mixed metal oxide may comprise Te and the element X may comprise Nb.

The three dimensional support of the catalyst comprises, a ceramic form selected from the group consisting of open or closed cell ceramic foams and ceramic monoliths. Furthermore, the ceramic form may comprise at least one material selected from the group consisting of: cordierite, alumina, zirconia, silica, aluminosilicate zeolites, phosphosilicate zeolites PSZ, and other zeolites.

The process may further comprise the step of feeding oxygen-containing gas to a first one of the at least two reaction zones. The separating step of the process may be performed by cooling the intermediate effluent stream such that at least a portion of the oxidation products condenses out of the intermediate effluent stream.

In one embodiment, the $C_3$ to $C_5$ alkane, $C_3$ to $C_5$ alkene, or mixture thereof may comprise propane, propene, or a mixture thereof and the oxidation product may comprise acrylic acid.

BRIEF DESCRIPTION OF THE DRAWINGS

A more complete understanding of the present invention will be gained from the embodiments discussed hereinafter and with reference to the accompanying drawings, in which like reference numbers indicate like features, and wherein.

DETAILED DESCRIPTION OF THE INVENTION

The process of the present invention is suitable for performing selective vapor phase catalytic oxidation of $C_3$ to $C_5$ alkanes and alkenes, and mixtures thereof, to their corresponding unsaturated carboxylic acids and unsaturated nitriles, including acrylic acid, methacrylic acid, acrylonitrile and methacrylonitrile. In this regard, the term vapor phase catalytic oxidation is intended to encompass simple oxidation, as well as ammoxidation and oxidative dehydrogenation.

To facilitate discussion, the efficacy of chemical reaction processes, including the process of the present invention, may be characterized in terms of the "feed conversion" and the "product yield". More particularly, feed conversion, or simply "conversion", is the percentage of the total moles of feed (e.g., $C_3$ to $C_5$ alkanes and alkenes, such as propane and propene, or a mixture thereof) that have been consumed by the reaction, regardless of what particular products were produced. The product yield, or simply "yield", is the percentage of the theoretical total moles of the desired product (e.g., unsaturated carboxylic acids or unsaturated nitrile, such as acrylic acid or acrylonitrile, respectively) that would have been formed if all of the feed had been converted to that product (as opposed to unwanted side products, e.g. acetic acid and $CO_x$ compounds). The aforesaid terms are generally defined as follows:

$$\text{feed conversion (\%)} = \frac{\text{moles of feed converted}}{\text{moles of feed supplied}} \times 100$$

$$\text{product yield (\%)} = \frac{\text{moles of product produced}}{\text{moles of feed supplied}} \times 100$$

As used herein, the term "$C_3$ to $C_5$ alkane" means a straight chain or branched chain alkane having from 3 to 5 carbons atoms per alkane molecule, for example, propane, butane and pentane. The term "$C_3$ to $C_5$ alkene" means a straight chain or branched chain alkene having from 3 to 5 carbons atoms per alkene molecule, for example, propene, butene and pentene. As used herein, the term "$C_3$ to $C_5$ alkanes and alkenes" includes both of the aforesaid alkanes and alkenes. Similarly, when used herein in conjunction with the terms "$C_3$ to $C_5$ alkane", or "$C_3$ to $C_5$ alkene", or "$C_3$ to $C_5$ alkanes and alkenes", the terminology "a mixture thereof", means a mixture that includes a straight chain or branched chain alkane having from 3 to 5 carbons atoms per alkane molecule and a straight chain or branched chain alkene having from 3 to 5 carbons atoms per alkene molecule, such as, without limitation, a mixture of propane and propene, or a mixture of n-butane and n-butene.

Figure 1:
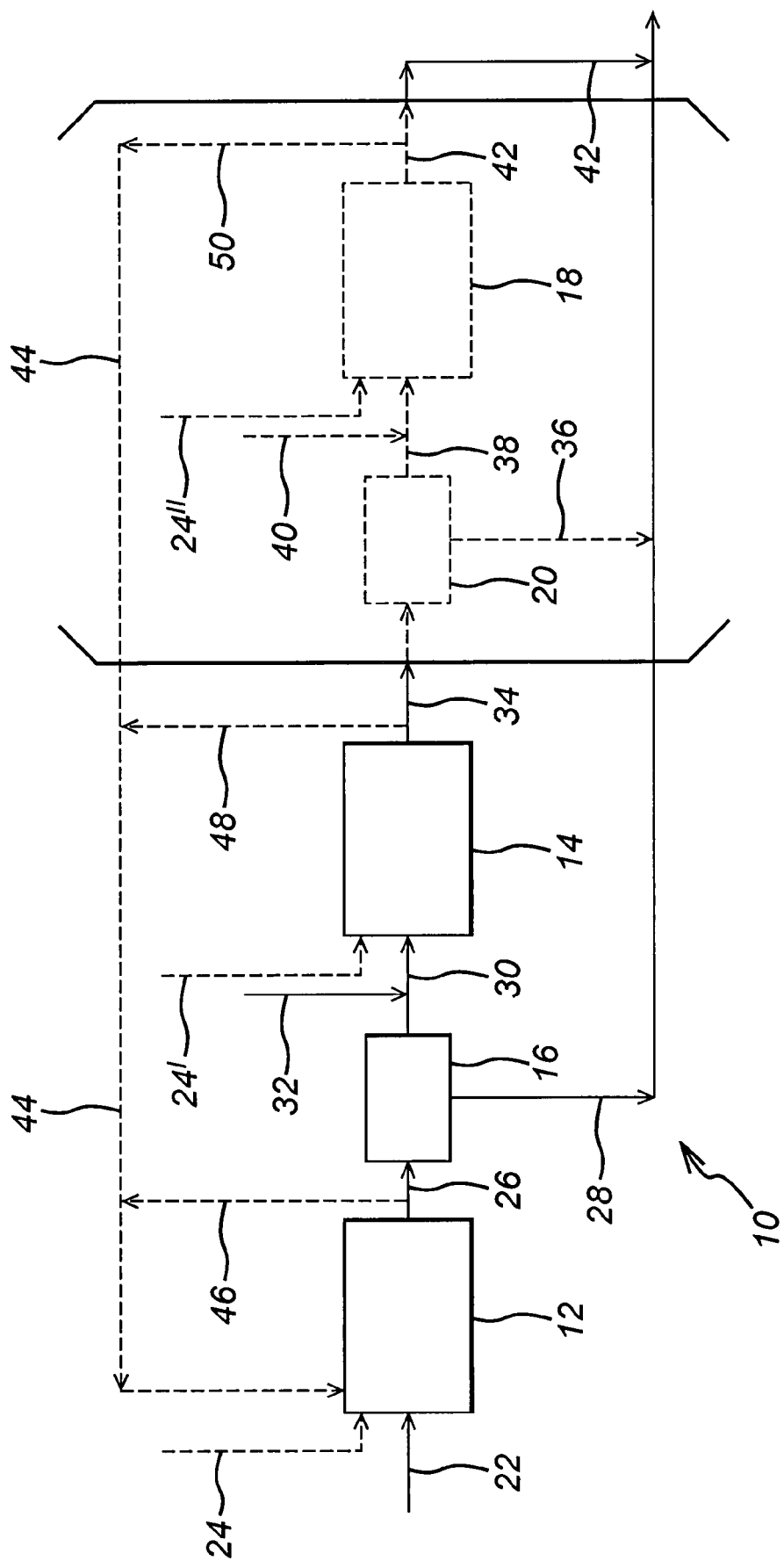
FIG. 1 is a schematic flow diagram of one embodiment of the process of the present invention.

With reference now to FIG. 1, a schematic representation is shown of a multi-stage catalytic vapor phase oxidation process 10, in accordance with the present invention, that is capable of converting a $C_3$ to $C_5$ alkane, a $C_3$ to $C_5$ alkene, or a mixture thereof (such as, for example, propane, or a mixture of propane and propene), to an unsaturated carboxylic acid (such as acrylic acid) or an unsaturated nitrile (such as acrylonitrile) in a single reaction step. The process 10 includes at least a first reaction zone (or "stage") 12 and a second reaction zone (or "stage") 14, which are arranged in series with one another such that the second reaction zone 14 is positioned downstream of the first reaction zone 12. The process 10 of the present invention also includes a separator, such as a condenser 16, which is positioned to intermediate the first and second reaction zones 12, 14, for a purpose to be described in detail hereinafter.

As shown in phantom in FIG. 1, the process 10 of the present invention may also include additional reaction zones, such as a third reaction zone (or "stage") 18 arranged in series with and downstream of the second reaction zone 14. Where the process 10 includes such additional reaction zones, it may also include additional separators, such as a second condenser 20 positioned intermediate the second and third reaction zones 14, 18, respectively, for a purpose to be described in detail hereinafter.

As used herein, an arrangement of reaction zones "in series" with one another means that the reaction zones are arranged such that at least a portion of the output stream of the first reaction zone forms at least a portion of the input stream of the second reaction zone and each successive reaction zone is similarly interconnected with the preceding reaction zone. It is noted that the portion of output stream which forms a portion of the input stream of each the successive reaction zone need not be the same with respect to amount, proportion, composition, temperature, etc., since these stream characteristics should be determined according to the requirements of the particular overall reaction system and each reaction zone, as would be readily determinable by those having ordinary skill in the art. In particular, it is noted that the reaction zones 12, 14, 18 of the present invention are arranged in series with one another, with the separators 16, 20 positioned intermediate to successive reaction zones, 12, 14 and 14, 18, respectively, for purposes which will become clear hereinafter.

Furthermore, the overall yield of oxidation product from such multiple reaction zone (i.e., "multi-stage") reaction systems is cumulative relative to each reaction zone. In other words, for example, where such a reaction system has three reaction zones and the first reaction zone provides an oxidation product yield of about 35%, the second reaction zone provides about 20% yield, and the third reaction zone provides about 10%, then the theoretical overall yield of oxidation product by the system could be expected to be about 65%. This staged oxygen arrangement has practical limitations since, as the hydrocarbons to be oxidized are consumed in successive stages, the additional oxidation product produced thereby will cease to be in amount significant enough to justify the additional reaction zones of the reactor system.

Any type of reactors that are suitable for performing the desired vapor phase oxidation reactions may be used to contain, or hold, the reaction zones 12, 14, 18 in accordance with the process 10 of the present invention. Shell-and-tube reactors, for example and without limitation, are suitable for use in connection with the process 10 of the present invention.

In addition, at least one catalyst bed (not shown, per se) is contained within each reaction zone 12, 14, 18 and comprises at least one supported catalyst (not shown per se), each of which is capable facilitating the desired vapor phase oxidation reaction. The catalyst beds may be of different types, including but not limited to fixed-bed, moving-bed and fluidized-bed.

Suitable catalysts compositions are readily selectable by persons of ordinary skill based upon the particular $C_3$ to $C_5$ alkane, $C_3$ to $C_5$ alkene, or mixture thereof, and the desired oxidation products. For example, suitable oxidation catalyst compositions for a variety of vapor phase oxidation reactions are described fully in each of U.S. Pat. Nos. 6,383,978, 6,403,525, 6,407,031, 6,407,280, 6,461,996, 6,472,552, 6,504,053, 6,589,907 and 6,624,111. Based on recent research, it appears that catalyst formulations which contain a mixed metal oxide comprising, as essential components, molybdenum (Mo) and vanadium (V) are particularly suitable for use in the process of the present invention—single-step vapor phase catalytic oxidation of alkanes, alkenes, and mixtures thereof to their corresponding unsaturated carboxylic acids and unsaturated nitriles.

More particularly, catalyst compositions suitable for use in the process of the present invention comprise a mixed metal oxide having the empirical formula $$Mo_a V_b N_c X_d O_e$$

wherein N is at least one element selected from the group consisting of Te and Se; X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein a, b, c, d and e are, respectively, the atomic ratios of molybdenum, vanadium, N, X and oxygen, and when a=1, b=0.01 to 1.0, c=0.01 to 1.0, d=0.01 to 1.0, and e is dependent on the oxidation state of the other elements.

For example, in one embodiment, when a=1, b=0.1 to 0.5, c=0.05 to 0.5 and d=0.01 to 0.5. In another embodiment, when a=1, b=0.15 to 0.45, c=0.05 to 0.45 and d=0.01 to 0.1. The value of e, i.e. the amount of oxygen present, is, of course, dependent on the oxidation state of the other elements present in the catalyst, and is typically in the range of from 3 to 4.7.

Additionally, in a particular embodiment of the present invention, the element N in the at least one catalyst may comprise Te, and the element X may comprise Nb. The aforesaid catalyst composition may further comprise a promoter element, such as, for example, nickel, palladium, copper, silver and gold.

It has also been found unexpectedly advantageous to combine the aforesaid catalyst composition with a three dimensional support, i.e., a support having dimensions along the x, y and z orthogonal axes of a Cartesian coordinate system, and providing a relatively high surface area per unit volume. Though lower and higher amounts are possible, in one embodiment, the support structure exhibits a surface area of 0.01 to 50 m²/g, such as, for example, 0.1 to 10 m²/g.

In one embodiment, the support structure may have a porous structure and exhibit a pore volume percent ranging from 1 to 95%, such as 5 to 80%, or even 10 to 50%. Such support structures permit relatively high feed velocities with insubstantial pressure drop.

Further, the support structure should be sufficiently strong to resist fracture under the weight of the catalyst, which can range up to almost 100% of the weight of the combination of the catalyst and the support structure. Typically, however, the support structure is at least 60 wt % of the weight of the combination, or even 70 to 99.99 wt % of the weight of the combination, including as much as 90 to 99.9 wt % of the weight of the combination.

The exact physical form of the support structure is not particularly important so long as it meets the above-noted general criteria. Examples of suitable physical forms include foam, honeycomb, lattice, mesh, monolith (single and multi-layer), woven fiber, non-woven fiber, gauze, perforated substrates (e.g., foil), particle compacts, fibrous mat and mixtures thereof. For these supports it will be appreciated that typically one or more open cells will be included in the structure. The cell size may vary as desired, as may the cell density, cell surface area, open frontal area and other corresponding dimensions. By way of example, one such structure may have an open frontal area of at least 75%. The cell shape may also vary and may include polygonal shapes, circles, ellipses, as well as others.

The support structure may be fabricated from a material that is inert to the reaction environment of the catalytic reaction. Suitable materials include, but are not limited to, ceramics such as cordierite, silica, alumina, silica-alumina, aluminosilicate, zirconia, titania, boria, mullite, alumina, lithium aluminum silicate, oxide-bonded silicon carbide or mixtures thereof.

The catalysts may be applied to the support structure using any suitable art-disclosed technique. For instance, the catalyst composition may be deposited on the surface of the support structure by coating, or deposited inside the support, by methods including impregnation, wash coating, slurry dip-coating, chemical vapor deposition (CVD), physical vapor deposition (PVD) and precipitation. Catalysts are typically applied to ceramic foams by chemical vapor deposition (CVD) and physical vapor deposition (PVD). The foam structures comprise specific numbers of pores per inch, such as, without limitation, 30 to 150 pores per inch. Catalysts are typically applied to ceramic monoliths by wash coating the monoliths with a solution, slurry, suspension or dispersion of catalyst material. The monoliths comprise specific numbers of cells per inch, such as, without limitation, 200 to 800 cells per inch. The ceramic supports having pores and cells permit high space velocity passage of reactants and products through and past the catalyst with a corresponding minimized pressure drop.

According to one exemplary embodiment, the structured catalysts are in the form of three-dimensional structures selected from the group consisting of metallic foams and metallic monoliths, extruded catalysts, membrane catalysts having permeable walls between openings, catalysts arranged in arrays, catalysts having openings including grooves, channels and other passages created by techniques including corrugation, stacking staggering and superimposing, fibrous catalysts, woven catalysts, mesh catalysts, non-woven catalysts, multi-layered catalysts joined together by a thermally conductive connection and coated with an oxidation barrier, and perforated ceramic and metallic disks. For example, without limitation, the three dimensional support may be selected from the group consisting of open or closed cell ceramic foams and ceramic monoliths comprising ceramics including cordierite, alumina, zirconia, silica, aluminosilicate zeolites, phosphosilicate zeolites PSZ, and other zeolites.

It will be appreciated, as to the support structures disclosed herein, that a plurality of layers may be employed, with each layer having the same or different structure, composition, orientation, or other characteristic relative to a previous layer. For instance, a catalyst bed may contain a stack or layers of fabric disks formed from ceramic oxide fabric supported catalysts or the fibrous ceramic composite catalysts. Individual layers may or may not be self-supporting. Preferably, however, the combination embodied in the overall structure is generally self-supporting. When employed herein, ceramic oxide fibers may be comprised of alumina, silica, boria, cordierite, magnesia, zirconia, or a combination of any of these oxides.

Suitable supported mixed metal oxide catalysts may be prepared as follows.

In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, M, N, X and O, as previously defined.

Suitable solvents include water; alcohols including, but not limited to, methanol, ethanol, propanol, and diols, etc.; as well as other polar solvents known in the art. Generally, water is most conveniently used. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed at the time of mixing.

For example, when a mixed metal oxide of the formula $Mo_aV_bTe_cNb_dO_e$ wherein the element N is Te and the element X is Nb, is to be prepared, an aqueous solution of niobium oxalate may be added to an aqueous solution or slurry of ammonium heptamolybdate, ammonium metavanadate and telluric acid, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mm Hg to 500 mm Hg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mm Hg to 760 mm Hg, for example, at a bath temperature of from 40° to 90° C. and at a pressure of from 10 mm Hg to 350 mm Hg, or even at a bath temperature of from 40° C. to 60° C. and at a pressure of from 10 mm Hg to 40 mm Hg. Air drying may be effected at temperatures ranging from 25° C. to 90° C. Rotary evaporation or air drying are generally preferred.

Once obtained, the catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination may be performed at a temperature of from 350° C. to 850° C., for example, from 400° C. to 700° C., or even from 500° C. to 640° C. The calcination is performed for an amount of time suitable to form the aforementioned catalyst. Typically, the calcination is performed for from 0.5 to 30 hours, such as from 1 to 25 hours, or from 1 to 15 hours, to obtain the desired mixed metal oxide catalyst composition.

In one method, calcination is performed in two stages. In the first stage, the catalyst precursor is calcined in an oxidizing environment (e.g., air) at a temperature of from 200° C. to 400° C., such as from 275° C. to 325° C. for from 15 minutes to 8 hours, or even for from 1 to 3 hours. In the second stage, the material from the first stage is calcined in a non-oxidizing environment (e.g., an inert atmosphere) at a temperature of from 500° C. to 750° C., such as for from 550° C. to 650° C., for 15 minutes to 8 hours, or even for from 1 to 3 hours. Optionally, a reducing gas, such as, for example, ammonia or hydrogen, may be added during the second stage calcination.

In another preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the aforesaid gaseous environments. Therefore, it is advantageous to conduct the calcination in a bed with continuous flow of the desired gas(es) through the bed of solid catalyst precursor particles.

The starting materials for the above mixed metal oxide catalyst composition are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities and is ready for application to the support structure. However, the mixed metal oxide may be converted to a catalyst having higher activities by performing various further treatment steps on the catalyst precursor, prior to calcination and application to the support structure.

For example, the catalyst precursor may be subjected to grinding. There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation. As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide, the viscosity, the concentration, etc., of the solvent used in the case of wet grinding, or the optimum conditions of the grinding apparatus. However, it is advantageous for grinding to be conducted until the average particle size of the ground catalyst precursor would usually be at most 20 µm, more preferably at most 5 µm. Improvement in the catalytic performance may occur due to such grinding.

Further, in some cases, it is possible to further improve the catalytic activities by adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

After the catalyst precursor has undergone all desired treatments, which may be prior to, during, or even after, calcination, it may be combined, i.e., loaded or coated onto, the support structure by any suitable method known to persons of ordinary kill. In one typical method, sometimes referred to generally as wash coating, solutions containing the constituent metals are contacted with the dry support structure such that the support is wetted; then, the resultant wetted material is dried, for example, at a temperature from room temperature to 200° C., followed by calcination as described above. In another method, metal solutions are contacted with the support, typically in volume ratios of greater than 3:1 (metal solution:support), and the solution agitated such that the metal ions are ion-exchanged onto the support. The metal-containing support is then dried and calcined as described above.

With reference now back to FIG. 1 and the multi-stage catalytic vapor phase oxidation process 10 of the present invention, separators suitable for use with the present invention include any suitable fluid separator capable of separating a gaseous product stream into a plurality of streams, according to composition, such as separating a gaseous output stream into a first stream containing primarily the desired reaction product(s) and a second stream containing primarily unreacted materials and by-products. For example, while not intending to be limited, the separator may be a partial condenser 16, 20, such as a conventional heat exchanger, capable of cooling the gaseous output stream sufficiently to condense and separate out at least a portion of the lowest boiling point components of the gaseous output stream would be suitable for use with the process 10 of the present invention. The coolant in such a condenser may be, for example, without limitation, cooling tower water having a temperature between 85° F. and 105° F. (29° C. to 40° C.), or chilled water having a temperature between 32° F. and 40° F. (0° C. and 5° C.). In addition, for example, the separators may include gas absorbers or gas adsorbers.

Suitable starting materials, which are discussed hereinafter and which are readily determinable by persons having ordinary skill in the art, are fed into the first reaction zone 12. In the first reaction zone 12, the starting materials come into contact with the catalyst and react with one another to form the desired oxidation products, as well as various side products and by-products, according to the particular types of $C_3$ to $C_5$ alkanes and alkenes used.

Suitable starting materials for the process 10 of the present invention depend upon the desired oxidation product and typically include, but are not limited to, a $C_3$ to $C_5$ alkane, a $C_3$ to $C_5$ alkene, or a mixture thereof, and an oxygen-containing gas, as well as, optionally, steam, diluting gases and ammonia. The starting materials may be added separately and simultaneously to the first reaction zone 12, or they may be mixed and fed to the first reaction zone 12 as one or more combined streams. For example, as explained in further detail hereinafter, the initial feed stream 22, shown in FIG. 1, may be a combined stream comprising an oxygen-containing gas and a $C_3$ to $C_5$ alkane, a $C_3$ to $C_5$ alkene, or a mixture thereof. The optional supplemental streams 24, 24', 24", shown in phantom in FIG. 1, may be, for example, steam-containing gases or ammonia-containing gases, depending upon the particular oxidation products desired. The optional supplemental streams 24, 24', 24" may even comprise additional $C_3$ to $C_5$ alkane, $C_3$ to $C_5$ alkene, or a mixture thereof.

The detailed mechanism of the oxidation reaction of the present invention is not clearly understood, but the oxidation reaction is carried out by oxygen atoms present in the above mixed metal oxide or by molecular oxygen present in the feed gas. Addition of oxygen-containing gas to the starting materials provides such molecular oxygen to the reaction system. The term "oxygen-containing gas," as used herein, refers to any gas comprising from 0.01% up to 100% oxygen, including, for example, air. Thus, although the oxygen-containing gas may be pure oxygen gas, it is usually more economical to use an oxygen-containing gas such as air, since purity is not particularly required.

The purity of the starting material, i.e., the $C_3$ to $C_5$ alkane, the $C_3$ to $C_5$ alkene, or the mixture thereof, is not particularly limited. Thus, commercial grades of such alkanes, or mixtures of such alkanes and alkenes, may be used as starting material for the process 10 of the present invention, although higher purities are advantageous from the standpoint of minimizing competing side reactions. In addition, mixed $C_3$ to $C_5$ alkane/alkene feeds are generally more easily obtained and may include price incentives (e.g., lower separation costs) relative to pure $C_3$ to $C_5$ alkane feeds. For example, a mixture of alkane and alkene containing a lower alkene such as ethene, a lower alkane such as methane or ethane, air or carbon dioxide, as impurities, may be used without any particular problem. Further, the starting material mixture of $C_3$ to $C_5$ alkane and alkene may be a mixture of various $C_3$ to $C_5$ alkanes and alkenes. Further details concerning the starting materials will be discussed hereinafter in connection with particular embodiments of the present invention.

Suitable diluting gases include, but are not limited to, one or more of: carbon monoxide, carbon dioxide, or mixtures thereof, an inert gas, such as nitrogen, argon, helium, or mixtures thereof. A suitable molar ratio of the starting materials for the initial feed stream 22, ($C_3$ to $C_5$ alkane, $C_3$ to $C_5$ alkene, or a mixture thereof):(oxygen):(diluting gas):($H_2O$), would be, for example, (1):(0.1 to 10):(0 to 20):(0.2 to 70), for example, including but not limited to, (1):(1 to 5.0):(0 to 10):(5 to 40).

Where it is desired to produce unsaturated carboxylic acids, it is beneficial to include steam among the starting materials. In such a case, for example, a gaseous input stream comprising a mixture of and oxygen-containing gas and a steam-containing $C_3$ to $C_5$ alkane, or a steam-containing $C_3$ to $C_5$ alkene, or a steam-containing mixture thereof, may be used. It is noted that the steam may be added to the first reaction zone 12 separately from the $C_3$ to $C_5$ alkane, the $C_3$ to $C_5$ alkene, or the mixture thereof, and the oxygen-containing gas, as an initial feed stream 22 and an optional steam stream 24, respectively (see FIG. 1). Alternatively, a steam-containing $C_3$ to $C_5$ alkane, or a steam-containing $C_3$ to $C_5$ alkene, or a steam-containing mixture thereof, and the oxygen-containing gas may be separately supplied to the first reaction zone 12. The steam to be employed may be present in the form of steam gas in the reaction system, and the manner of its introduction is not particularly limited.

When steam is supplied together with the mixture of $C_3$ to $C_5$ alkanes and alkenes, as starting material gas, the selectivity for an unsaturated carboxylic acid is distinctly improved, and the unsaturated carboxylic acid can be obtained in good yield. However, the conventional technique utilizes a diluting gas, as described above, for the purpose of diluting the starting material. Such a diluting gas is used to adjust the space velocity, the oxygen partial pressure and the steam partial pressure, as will be readily understood by persons having ordinary skill in the art.

Where it is desired to produce unsaturated nitriles, the starting materials must include ammonia. In such cases, it is possible to use an initial feed stream 22 which is a gas mixture comprising a $C_3$ to $C_5$ alkane, a $C_3$ to $C_5$ alkane, or a mixture thereof, ammonia (not shown), and an oxygen-containing gas. Alternatively, an oxygen-containing gas and a gaseous mixture comprising a $C_3$ to $C_5$ alkane, or a $C_3$ to $C_5$ alkene or a mixture thereof, and ammonia may be supplied as separate feed streams (not shown) to the first reaction zone 12.

In the process 10 of the present invention, as the starting material mixture of $C_3$ to $C_5$ alkanes and alkenes, it is suitable to use a mixture of $C_3$ to $C_5$ alkane and $C_3$ to $C_5$ alkene, for example, propane and propene, isobutane and isobutene, or n-butane and n-butene. According to the present invention, from such a mixture of an alkene and an alkane, an unsaturated carboxylic acid such as an α,β-unsaturated carboxylic acid can be obtained in good yield. For example, when propane and propene, or isobutane and isobutene, are used as the starting material mixture of alkane and alkene, acrylic acid or methacrylic acid will be obtained, respectively, in good yield. In the mixture of alkane and alkene, the alkane is present in an amount of at least 0.5% by weight up to 95% by weight, preferably at least 0.5% by weight to 10% by weight; most preferably, 0.5% by weight to 5% by weight.

As an alternative, an alkanol, such as isobutanol, which will dehydrate under the reaction conditions to form its corresponding alkene, i.e. isobutene, may also be used as a feed material to the present process or in conjunction with the previously mentioned feed streams. Suitable alkanols include, but are not limited to, normal and branched alcohols, alkyl halides, amines and other functionalized alkanes, including, but not limited to, ethanol, n- or iso-propanol, and n- or branched butanols.

It is also possible to operate the process 10 of the present invention using only a $C_3$ to $C_5$ alkane, a $C_3$ to $C_5$ alkene, or a mixture thereof, substantially in the absence of molecular oxygen. In such a case, it is preferred to adopt a method wherein a part of the catalyst is appropriately withdrawn from the reaction zone from time to time, then sent to an oxidation regenerator, regenerated and then returned to the reaction zone(s) for reuse. As the regeneration method of the catalyst, a method may, for example, be employed which comprises contacting an oxidative gas such as oxygen, air or nitrogen monoxide with the catalyst in the regenerator usually at a temperature of from 300° to 600° C.

With reference again to FIG. 1, a first effluent stream 26 exits the first reaction zone 12 and typically contains, but is not limited to, one or more oxidation products (e.g., unsaturated carboxylic acids and unsaturated nitriles), unreacted oxygen, and unreacted $C_3$ to $C_5$ alkane or alkene, or mixture thereof and, possibly, unreacted water and unreacted ammonia, depending upon the starting materials used. The first effluent stream 26 also typically contains reaction by-products, including for example, but not limited to, acetic acid and carbon dioxide.

In accordance with the present invention, at least a portion of the one or more oxidation products is separated from the first effluent stream 26, for example, by using a separator, such as the condenser 16 shown in FIG. 1, to produce an intermediate product stream 28 and an intermediate feed stream 30 (see FIG. 1). The intermediate product stream 28 typically contains, but is not limited to, at least a portion of the one or more oxidation products from the first effluent stream 26, as well as other condensables, such as organic acids, aldehydes, ketones, and water. The intermediate product stream 28 may be fed to additional processing apparatus (not shown) to undergo further separation and purification processes. The intermediate feed stream 30 contains, but is not limited to, at least a portion of the unreacted oxygen, unreacted $C_3$ to $C_5$ alkane or alkene, or mixture thereof, and possibly reaction by-products such as acetic acid and carbon dioxide, and, possibly, unreacted water and unreacted ammonia, depending upon the starting materials used.

As shown in FIG. 1, the intermediate feed stream 30 is fed into the second reaction zone 14, along with additional oxygen-containing gas 32. More particularly, the additional oxygen-containing gas 32 may be first combined with the intermediate feed stream 30 and then fed together, as a combined stream (see FIG. 1) to the second reaction zone 14. Alternatively, the additional oxygen-containing gas 32 may be fed to the second reaction zone 14 as a separate feed stream (not shown). In the second reaction zone 14, the unreacted $C_3$ to $C_5$ alkane or alkene, or mixture thereof, and the oxygen (including the unreacted oxygen already present in the intermediate feed stream 30, as well as the additional oxygen contributed by the oxygen-containing gas 32) come into contact with the at least one catalyst in the second reaction zone 14 and react with one another to form the desired oxidation products, as well as various side products and by-products, according to the particular types of alkanes and alkenes used.

A second effluent stream 34 (see FIG. 1) exits the second reaction zone 14 and typically contains, but is not limited to, one or more oxidation products (e.g., unsaturated carboxylic acid and unsaturated nitrile), unreacted oxygen, and unreacted $C_3$ to $C_5$ alkane or alkene, or mixture thereof, as well as reaction by-products which may include, but are not limited to, acetic acid and carbon dioxide and, possibly, unreacted water and unreacted ammonia, depending upon the starting materials used. The second effluent stream 34 may be fed to additional processing apparatus (not shown) to undergo separation and purification processes, as is well-known to persons having ordinary skill in the art, to recover the one or more oxidation products.

The cumulative yield (%) of a particular oxidation product produced by a multi-stage oxidation reaction process, such as the process 10 of the present invention, is calculated by adding the numbers of moles of the particular oxidation product present in each of the effluent streams, dividing this sum by the number of moles of alkane (or alkane and alkene) fed to the process, and multiplying the result by 100. For example, the following formula is suitable for calculating the cumulative yield of oxidation product for the above-described process), which has a first reaction zone 12 and a second reaction zone 14:

$$\text{product yield (\%)} = \frac{\text{moles of product in first effluent stream} + \text{moles of product in second effluent stream}}{\text{moles of feed supplied}} \times 100$$

The cumulative yield of the desired oxidation product produced by the above-described process 10 in accordance with the present invention is greater than the cumulative yield of the desired oxidation product that is produced by a process that does not include both separating at least a portion of the one or more oxidation products from the first effluent stream 26, as well as feeding additional oxygen-containing gas 32 to the second reaction zone 14. In addition, the cumulative yield of the one or more oxidation products produced by the above-described process 10 in accordance with the present invention is greater than the cumulative yield of the one or more oxidation products that is produced by a process that includes only feeding additional oxygen-containing gas 32 to the second reaction zone 14, without separating at least a portion of the one or more oxidation products from the first effluent stream 26. The process 10 of the present invention allows for the use of starting materials containing a higher concentration of the $C_3$ to $C_5$ alkane, the $C_3$ to $C_5$ alkene, or mixture thereof. It is also believed that a greater portion of the oxygen in each subsequent reaction remains available for reacting and converting the $C_3$ to $C_5$ alkanes and alkenes.

With reference again to FIG. 1, and particularly the features shown in phantom, in another embodiment of the present invention, at least a portion of the one or more oxidation products are separated from the second effluent stream 34, for example, by using a second separator, such as the second condenser 20 shown in phantom in FIG. 1, to produce a second intermediate product stream 36 and a second intermediate feed stream 38 (shown in phantom in FIG. 1). The second intermediate product stream 36 typically contains, but is not limited to, at least a portion of the one or more oxidation products from the second effluent stream 34, as well as other condensables, such as organic acids, aldehydes, ketones, and water. The second intermediate product stream 36 may be fed to additional processing apparatus (not shown) to undergo further separation and purification processes. The second intermediate feed stream 38 contains, but is not limited to, at least a portion of the unreacted oxygen, unreacted $C_3$ to $C_5$ alkane or alkene, or mixture thereof, and possibly reaction by-products such as acetic acid and carbon dioxide such as acetic acid and carbon dioxide, and, possibly, unreacted water and unreacted ammonia, depending upon the starting materials used.

As shown in phantom in FIG. 1, the second intermediate feed stream 38 is fed into the third reaction zone 18 (shown in phantom), along with additional oxygen-containing gas 40. More particularly, the additional oxygen-containing gas 40 may be first combined with the second intermediate feed stream 38 and then fed together, as a combined stream (see FIG. 1) to the third reaction zone 18. Alternatively, the additional oxygen-containing gas 40 may be fed to the third reaction zone 18 as a separate feed stream (not shown). In the third reaction zone 18, the unreacted $C_3$ to $C_5$ alkane or alkene, or mixture thereof, and the oxygen (including the unreacted oxygen already present in the second intermediate feed stream 38 and the additional oxygen contributed by the oxygen-containing gas 32) come into contact with the at least one catalyst in the third reaction zone 18 and react with one another to form the desired oxidation products, as well as various side products and by-products, according to the particular types of alkanes and alkenes used.

A third effluent stream 42 (see FIG. 1) exits the third reaction zone 18 and typically contains, but is not limited to, one or more oxidation products (e.g., unsaturated carboxylic acid and unsaturated nitrile), unreacted oxygen, and unreacted $C_3$ to $C_5$ alkane or alkene, or mixture thereof, as well as reaction by-products which may include, but are not limited to, acetic acid and carbon dioxide. The third effluent stream may also contain, possibly, unreacted water and unreacted ammonia, depending upon the starting materials used. The third effluent stream 42 may be fed to additional processing apparatus (not shown) to undergo separation and purification processes, to recover the one or more oxidation products.

It is noted that the process 10 of the present invention may be suitably operated as a single-pass reaction or, alternatively, with recycle to one or more of the reaction zones 12, 14, 18, without losing the benefits achieved by the present invention. More particularly, by a single-pass vapor phase catalytic oxidation reaction is meant a vapor phase catalytic oxidation reaction wherein the reactants only pass through each of the reaction zones 12, 14, 18, i.e. over and/or through the catalyst beds, one time. There is no recycle of any unreacted reactants nor is there any recycle of reacted materials, regardless of whether they are products or by-products of the reaction. On the other hand, a vapor phase catalytic oxidation reaction with recycle would involve sending a recycle stream (shown in phantom 44) comprising at least a portion (shown in phantom 46, 48, 50) of the effluent streams 26, 34, 42, respectively, of one or more of the reaction zones 12, 14, 18, respectively, back to one or more of the reaction zones 12, 14, 18.

Figure 2:
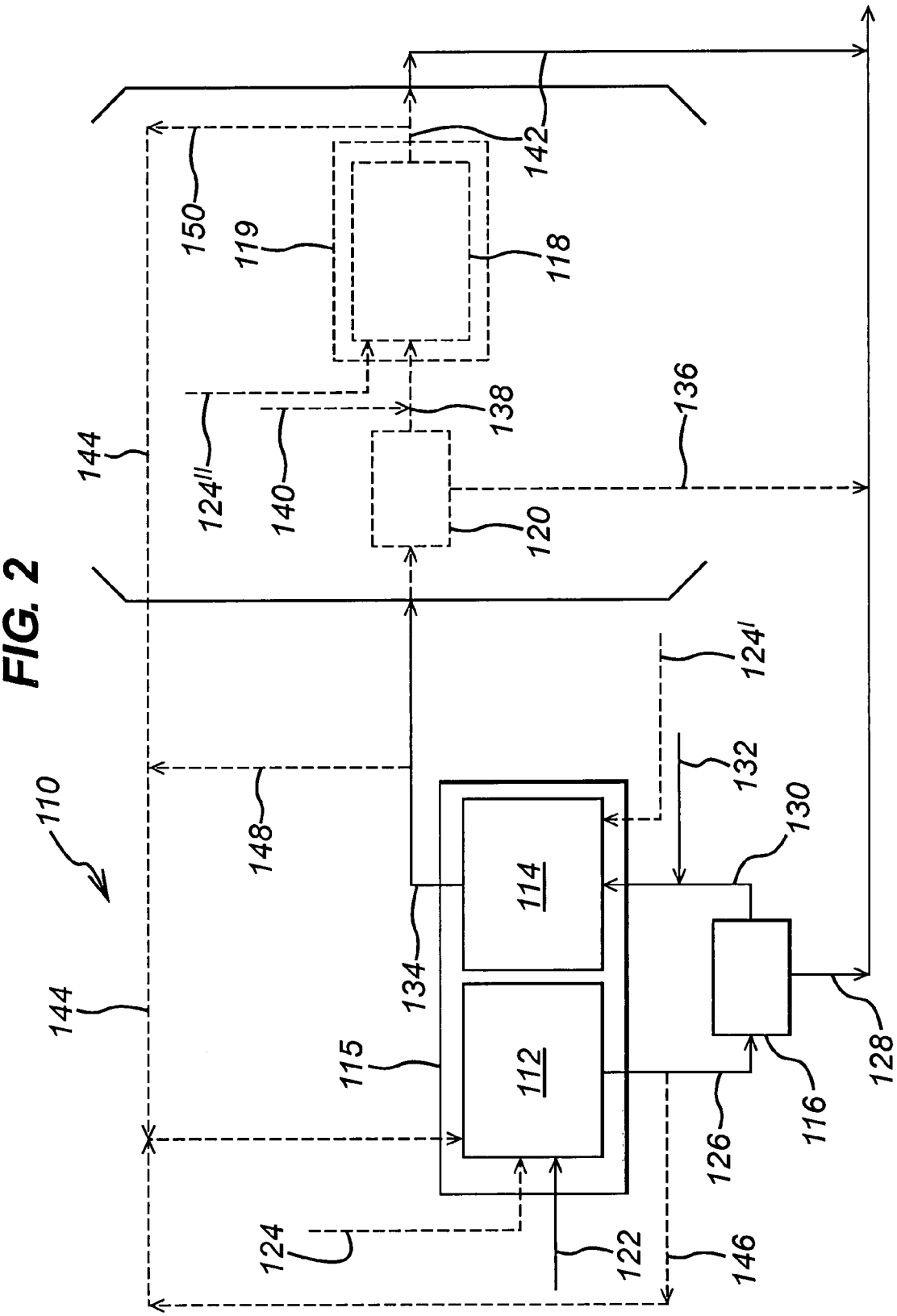
FIG. 2 is a schematic flow diagram of another embodiment of the process of the present invention.

With reference to FIG. 2, it is noted that elements illustrated in FIG. 2, which correspond to the elements described above with respect to FIG. 1, have been designated by corresponding reference numerals increased by one hundred. The alternative embodiment of FIG. 2, as well as the various elements thereof, are constructed and designated for use in substantially the same manner as the embodiment of FIG. 1 and the elements thereof, unless otherwise stated.

FIG. 2 shows an alternative embodiment of the process of the present invention that utilizes fewer reaction vessels because multiple reaction zones are contained within a single reaction vessel. More particularly, a reactor vessel 115 may be adapted to be capable of containing a plurality of reaction zones, such as first and second reaction zones 112, 114. Such a reactor vessel 115 may, for example, include an interior baffle or manifold (not shown) which divides the interior of the reaction vessel 115 into two separate heat exchange zones (not shown), i.e., one for each reaction zone 112, 114. Where the reactor vessel 115 is a shell and tube type of reactor, a first half of the tubes therein (not shown) may extend through one heat exchange zone of the reactor vessel 115 and the second half of the tubes (not shown) may extend through the other heat exchange zone. Each half of the tubes, respectively, of such a reaction vessel 115 contains a reaction zone. For example, the first half of the tubes might contain the first reaction zone 112, and the second half of the tubes would contain the second reaction zone 114. This arrangement of equipment conserves capital by requiring only one reactor vessel 115, rather than two or more, to contain two or more reaction zones. The design and construction of such reactor vessels having multiple reaction zones are well within the skill of persons having ordinary skill in the art.

With reference still to FIG. 2, in operation, the feed materials, as described hereinabove (i.e., including at least a $C_3$ to $C_5$ alkane, a $C_3$ to $C_5$ alkene, or a mixture thereof), is directed into the first half of the tubes and pass through the first reaction zone 112. As described previously hereinabove in connection with the first embodiment shown in FIG. 1, in the first reaction zone 112, the starting materials come into contact with a suitable catalyst situated therein, and react with one another to form the desired oxidation products, as well as various side products and by-products, according to the particular types of $C_3$ to $C_5$ alkanes and alkenes used. A first effluent stream 126 exits from the first half of the tubes and the reaction vessel 115 and is fed to a first separator, such as a first inter-condenser 116. The first inter-condenser 116 separates the first effluent stream 126 into a first intermediate product stream 128 and a first intermediate feed stream 130.

The first intermediate feed stream 130, which contains unreacted $C_3$ to $C_5$ alkanes or alkenes, or mixtures thereof, among other things, is then directed back into the reaction vessel 115 and the second half of the tubes, along with additional oxygen-containing gas 132. The unreacted $C_3$ to $C_5$ alkanes or alkenes, or mixtures thereof, and the additional oxygen-containing gas 132 pass through the second reaction zone 114, wherein they come into contact with a suitable catalyst situated therein, and react with one another to form the desired oxidation products, as well as various side products and by-products, according to the particular types of $C_3$ to $C_5$ alkanes and alkenes used. A second effluent stream 134 exits from the second half of the tubes and the reaction vessel 115, and passes through a second separator, such as a second inter-condenser 120. The second inter-condenser 120 separates the second effluent stream 134 into a second intermediate product stream 136 and a second intermediate feed stream 138.

The second intermediate feed stream 138, which contains unreacted $C_3$ to $C_5$ alkanes or alkenes, or mixtures thereof, among other things, may then, optionally, be fed, along with additional oxygen-containing gas 140, to a third reaction zone 118 for reaction of unreacted feed materials (i.e., unreacted $C_3$ to $C_5$ alkane or alkene, or mixture thereof, and unreacted oxygen, etc) in the manner described hereinabove in connection with FIG. 1. The third reaction zone 118 may be contained within a second, separate reactor vessel 119 by itself, as shown schematically in FIG. 2. Alternatively, the reaction vessel 119 may contain all three reaction zones 112, 114, 118 (not shown), or the third reaction zone 118 and an optional fourth reaction zone (not shown). As will be readily apparent, many variations beyond those suggested here are possible and would be well within the skill of persons of ordinary skill to design and construct.

In a manner similar to that described hereinabove in connection with FIG. 1 and the first embodiment of the present invention, optional supplemental streams 124, 124', 124", shown in phantom in FIG. 2, may be, for example, steam-containing gases or ammonia-containing gases, depending upon the particular oxidation products desired. The optional supplemental streams 124, 124', 124" may even comprise additional $C_3$ to $C_5$ alkane, $C_3$ to $C_5$ alkene, or a mixture thereof.

Notwithstanding the broad applicability of the present invention, and without intending to limit the present invention in any way, a first application of the present invention will be described in further detail with respect to a case where propene and propane are used as the starting material mixture of alkene and alkane and air is used as the oxygen source to produce acrylic acid by vapor phase oxidation, in a single step, in the presence of a suitable mixed metal oxide catalyst. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propene/propane mixture, whereby high selectivity for acrylic acid can be obtained. This reaction can be conducted usually under atmospheric pressure, but may be conducted under a slightly elevated pressure or slightly reduced pressure. With respect to other mixtures of alkene(s) and alkane(s), the composition of the feed gas may be selected in accordance with the conditions for the mixture of propene and propane. For example, the feed streams to each reaction zone 12, 14, 18 may be as follows: propane in an amount between 3 vol % and 50 vol %, such as between 7 vol % and 25 vol %, oxygen in an amount between 1 vol % and 50 vol %, such as between 5 vol % and 25 vol %, and water (steam) in an amount between 1 vol % and 50 vol %, such as 5 vol % and 25 vol %, based upon the total volume of the particular feed stream. It is noted that the compositions of the various feed streams of the process 10 need not be the same as one another in order to realize the benefits of the present invention and, in fact, may need to be different from one another, as will be readily understood and determinable by persons of ordinary skill in the art.

Typical reaction conditions for the oxidation of propane or isobutane to acrylic or methacrylic acid may be utilized in the practice of the present invention. General conditions for the process of the present invention are as follows: the reaction temperature can vary from 200° C. to 700° C., but is usually in the range of from 200° C. to 550° C., for example, 300° C. to 450° C., or even 350° C. to 400° C.; the gas space velocity, "SV", in the vapor phase reactor is usually within a range of from 100 to 10,000 $hr^{-1}$, for example, 300 to 6,000 $hr^{-1}$, or even 300 to 2,000 $hr^{-1}$; the average contact time with the catalyst can be from 0.01 to 10 seconds or more, but is usually in the range of from 0.1 to 10 seconds, for example from 2 to 6 seconds; the residence time in each reaction zone can be between 0.5 and 5 seconds, such as between 1 and 3 seconds; the pressure in the reaction zone usually ranges from 0 to 75 psig, such as, for example, no more than 50 psig.

Of course, in the process 10 of the present invention, it is important that the hydrocarbon (i.e., $C_3$ to $C_5$ alkane, or a mixture of $C_3$ to $C_5$ alkanes and an alkenes) and oxygen concentrations in the various gas streams be maintained at the appropriate levels to minimize or avoid entering a flammable regime within the reaction zones 12, 14, 18 or especially in the effluent streams 26, 34, 42 of the reaction zones 12, 14, 18. For example, it is preferred that the oxygen concentration in the effluent streams 26, 34, 42 be relatively low to minimize after-burning. In addition, operation of the reaction zones 12, 14, 18 at a low temperature (for example, below 450° C.) is extremely attractive because after-burning becomes less of a problem, which enables the attainment of higher selectivity to the desired oxidation products. The catalysts suitable for use in connection with the process 10 of the present invention, as described hereinabove, typically operate more efficiently at the lower temperature range set forth above, significantly reducing the formation of by-products (such as, but not limited to, acetic acid and carbon oxides), and increasing selectivity to the desired oxidation product (for example, but not limited to, acrylic acid). As a diluting gas, to adjust the space velocity and the oxygen partial pressure, an inert gas such as nitrogen, argon or helium may be employed.

When the process 10 of the present invention is employed to perform oxidation reaction of propane and propene, in accordance with the present invention, carbon monoxide, carbon dioxide, acetic acid, etc. may be produced as by-products, in addition to acrylic acid. The effluent streams 26, 34, 42 and, therefore, the intermediate feed streams 30, 38 also, are likely to contain unreacted water. In addition, an unsaturated aldehyde may sometimes be formed, depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it to a vapor phase catalytic oxidation reaction with a conventional oxidation reaction catalyst for an unsaturated aldehyde.

Without intending to limit the present invention in any way, another application of the process 10 of the present invention is to produce an unsaturated nitrile. Such a process comprises reacting a $C_3$ to $C_5$ alkane, or a mixture of $C_3$ to $C_5$ alkanes and an alkenes, containing at least 0.5% by weight of the $C_3$ to $C_5$ alkane, with ammonia in the presence of a suitable catalyst, as described hereinabove, to produce an unsaturated nitrile by vapor phase oxidation, in a single step.

In the production of such an unsaturated nitrile, as the starting material alkane, it is preferred to employ a $C_3$ to $C_5$ alkane such as ethane, propane, butane, isobutane, or pentane. However, in view of the industrial application of nitriles to be produced, it is preferred to employ a lower alkane having 3 or 4 carbon atoms, particularly propane and isobutane.

Similarly, as the starting material mixture of alkane and alkene, it is preferred to employ a mixture of a $C_3$ to $C_5$ alkane and a $C_3$ to $C_5$ alkene, such as propane and propene, butane and butene, isobutane and isobutene, or pentane and pentene. However, in view of the industrial application of nitriles to be produced, it is more preferred to employ a mixture of a lower alkane having 3 or 4 carbon atoms and a lower alkene having 3 or 4 carbon atoms, particularly propane and propene, or isobutane and isobutene. For example, without limitation, in the mixture of alkane and alkene, the alkane may be present in an amount of at least 0.1% by weight up to 95% by weight, including at least 0.5% by weight to 10% by weight, or even 0.5% by weight to 5% by weight, based on the total weight of the starting material mixture.

The purity of the starting material alkane is not particularly limited, and an alkane containing a lower alkane, such as methane, ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkane, such as methane, ethane, a lower alkene such as ethene, air or carbon dioxide, as impurities, may be used without any particular problem. Further, the starting material mixture of alkane and alkene may be a mixture of various alkanes and alkenes.

There is no limitation on the source of the alkane. It may be purchased, per se, or in admixture with an alkene and/or other impurities. Alternatively, it can be obtained as a by-product of alkane oxidation. Similarly, there is no limitation on the source of the alkene. It may be purchased, per se, or in admixture with an alkane and/or other impurities. Moreover, the alkane, regardless of source, and the alkene, regardless of source, may be blended as desired.

The detailed mechanism of the oxidation reaction of this embodiment of the present invention is not clearly understood. When it is desired to incorporate molecular oxygen in the starting materials, the oxygen-containing gas may be pure oxygen gas. However, since high purity is not required, it is usually economical to use air as the oxygen-containing gas.

It is possible to utilize an initial feed stream 22 which is a gas mixture comprising an alkane, or a mixture of an alkane and an alkene, ammonia and an oxygen-containing gas. However, a gas mixture comprising an alkane, or a mixture of an alkane and an alkene and ammonia, and an oxygen-containing gas may be supplied separately, or alternately, as one or more feed streams.

When the process 10 of the present invention is operated using an alkane, or a mixture of an alkane and an alkene, and ammonia that is substantially free from molecular oxygen, as the feed gas, one may employ a method wherein a part of the catalyst is periodically withdrawn and sent to an oxidation regenerator for regeneration, and the regenerated catalyst is returned to the reaction zone. As a method for regenerating the catalyst, for example, without limitation, an oxidizing gas such as oxygen, air or nitrogen monoxide may be permitted to flow through the catalyst in the regenerator usually at a temperature of from 300° C. to 600° C.

It is noted that where acrylonitrile is the desired oxidation product, the proportion of air to be supplied to the reaction zones 12, 14, 18 is important with respect to the selectivity for acrylonitrile. Namely, high selectivity for acrylonitrile is obtained when air is supplied within a range of at most 25 moles, particularly 1 to 15 moles, per mole of the propane. Moreover, the proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the aforesaid conditions for propane.

The process of this alternate embodiment of the present invention may be conducted at a temperature of, for example, from 200° C. to 480° C., such as from 250° C. to 450° C., or even from 275° C. to 400° C. The gas space velocity, SV, in each of the reaction zones 12, 14, 18 is usually within the range of from 100 to 10,000 $hr^{-1}$, such as from 300 to 6,000 $hr^{-1}$, or even from 300 to 2,000 $hr^1$. The residence time of the reactants in each reaction zone can be between 0.5 and 5 seconds, such as between 1 and 3 seconds. As a diluent gas, for adjusting the space velocity and the oxygen partial pressure, there may be used carbon monoxide, carbon dioxide or mixtures thereof; an inert gas such as nitrogen, argon, helium or mixtures thereof; or mixtures thereof. When ammoxidation of propene is conducted using the process 10 of the present invention, in addition to acrylonitrile, carbon monoxide, carbon dioxide, acetonitrile, hydrocyanic acid and acrolein may form as by-products. During operation of the process 10 of the present invention to produce unsaturated nitriles, the effluent streams 26, 34, 42 and, therefore, the intermediate feed streams 30, 38 also, are likely to contain unreacted ammonia.

In the following Examples, "propane conversion" is synonymous with "feed conversion" and was calculated in accordance with the formulas provided earlier hereinabove. Furthermore, "AA yield" means acrylic acid yield and is synonymous with "product yield" and was calculated in accordance with the formulas provided earlier hereinabove.

Unless otherwise specified, all percentages recited in the following examples are by volume, based on the total volume of the feed or product gas stream.

The same mixed metal oxide catalyst composition, either without or with support material, is used for all of the following examples, and is prepared as follows.

An MoN/Te/Nb mixed metal oxide catalyst ("MMO Catalyst") was prepared in accordance with the techniques described in the present specification and used as the active catalyst ingredient. More particularly, an aqueous solution of niobium oxalate was added to an aqueous solution of ammonium heptamolybdate, ammonium metavanadate and telluric acid in proportions so that the atomic ratio of the respective metal elements were in the prescribed proportions. The water was then removed by rotary evaporation. The resulting precursor solid was calcined and then cryo-ground and extracted with oxalic acid.

The MMO Catalyst was further prepared and wash coated onto various solid three dimensional supports, including cordierite monoliths (obtained from Corning), steatite spheres and mullite-cordierite monoliths, as follows. The MMO Catalyst was ground and sieved to obtain particle sizes ranging between 10-25 microns. A solvent, i.e., de-ionized water, was then used to prepare a solution containing 20-25 wt % suspended catalyst particles. The solution was stirred constantly during wash coating to prevent sedimentation of the catalyst particles.

To wash coat the monolith supports, a piece of the monolith was completely immersed in the catalyst solution for a time between 30 seconds and one minute. The coated monolith was removed and gently shaken and air-blown to clear excess liquid in the channels. For supports of other shapes (such as the spheres), the solution was manually applied dropwise to the support in a manual or mechanical shaker.

In either case, drying was performed at 80-100° C. in a rotating heated oven for 15-30 minutes between each application. About three to five applications were needed to load 20-25 wt % of catalyst on a given support. The wt % of catalyst on support provided in Tables 1 and 2 was calculated as follows: [(final wt−initial wt of support)/final wt]×100.

All catalysts were tested in a laboratory reactor designed for single-pass one-step partial oxidation of propane to form acrylic acid, with a feed stream comprising 1 mole % propane mixed in air. Residence time was approximately 3 seconds and reaction temperatures are from 340-410° C. Products were analyzed by on-line Fourier Transform Infra-Red (FTIR) sampling.

EXAMPLE 1

Performance of MMO Catalyst Loaded on Cordierite Support

Unsupported MMO Catalyst (A, B, E and F) and MMO Catalyst supported on cordierite monoliths (C, D, G and H) were loaded, separately for each run, into the laboratory reactor for partial oxidation of propane to acrylic acid. The weight percent (wt %) and mass of MMO Catalyst present in the reactor for each run and the oxidation results are presented in Table 1 below. The data in Table 1 are organized (i.e., A, B, C and D together, and E, F, G and H together) for comparison at constant propane and oxygen conversion levels. The data in Table 1 demonstrate that the MMO Catalyst can be successfully wash coated onto a support material such as cordierite at the 20-35 wt % loading level. For oxidation of propane, the supported MMO Catalyst (C, D, G and H) provided acrylic acid yields that were comparable to those provided by the pure, unsupported MMO Catalyst (A, B, E and F), particularly when compared at similar active catalyst loadings and at constant propane or oxygen conversions. Surprisingly, little catalytic performance (e.g. acrylic acid yield and selectivity) was lost notwithstanding the fact that the mass of supported MMO Catalyst (C, D, G and H) in the reactor was significantly less than half the mass of unsupported MMO Catalyst (A, B, E and F) used in the reactor.

TABLE 1

Performance of MMO Catalyst unsupported and supported on cordierite (Corning).

| Run | % MMO Catalyst (support) | Wt MMO in reactor, g | Temp., ° C. | Propane Conv., % | $O_2$ conv., % | Acrylic Acid sel., % | Acrylic Acid yield, % |
|---|---|---|---|---|---|---|---|
| A | 100% MMO (unsupported base material) | 5.4 | 349 | 66.1 | 67.8 | 77.6 | 51.3 |
| B | 100% MMO (unsupported base material) | 2.2 | 400 | 66.5 | 84.1 | 72.9 | 48.5 |
| C | 23 wt % MMO supported on cordierite | 2.2 | 399 | 66.3 | 74.2 | 75.0 | 49.7 |
| D | 32 wt % MMO supported on cordierite | 3.4 | n/a | 64.8 | 72.0 | 74.2 | 48.1 |
| E | 100% MMO (unsupported base material) | 5.4 | 365 | 77.2 | 85.1 | 74.1 | 57.2 |
| F | 100% MMO (unsupported base material) | 2.2 | 402 | 67.5 | 84.6 | 70.8 | 47.8 |
| G | 23 wt % MMO supported on cordierite | 2.2 | 405 | 72.1 | 84.8 | 71.7 | 51.7 |
| H | 32 wt % MMO supported on cordierite | 3.4 | n/a | 73.6 | 87.4 | 71.7 | 52.8 |

EXAMPLE 2

Performance of MMO Catalyst Wash-Coated onto Supports of Different Shape and Composition The weight percent (wt %) and mass of MMO Catalyst, as well as the type of three dimensional support, which were present in the reactor for each run and the corresponding oxidation results are presented in Table 2 below. The data presented in Table 2 below demonstrate that excellent performing catalysts were prepared by wash coating the MMO Catalyst onto various three dimensional supports, including monoliths and spheres, with different compositions such as cordierite, steatite and mullite.

| Run | Catalyst/Support | Wt MMO in reactor, g | Temp, °C. | Propane conv., % | Acrylic Acid yield, % |
|---|---|---|---|---|---|
| J | 100% base MMO material | 5.4 | | | 60.0 |
| K | 36.5% MMO/stacked 600 & 400 CPSI monoliths (Corning) | 1.5 | 368 | 65.0 | 45.5 |
| L | 100% MMO/stacked 600 & 400 CPSI monoliths (Corning) | 5.4 | 352 | 63.7 | 50.1 |
| M | 15% MMO/steatite spheres (Saint Gobain) | 2.9 | 357 | 61.9 | 42.4 |
| N | 15% MMO/steatite spheres (Saint Gobain) | 2.9 | 373 | 94.0 | 51.0 |
| O | 35% MMO/mullite-cordierite (Corning) | 2.2 | 406 | 69.7 | 53.0 |

For all the following examples, a two-stage reaction process (i.e., an apparatus having a first reaction zone and a second reaction zone in series with the first reaction zone) was used to perform vapor phase catalytic oxidation of propane (alkane) to acrylic acid (unsaturated carboxylic acid). Each of the reaction zones was packed with the same volume of the above-described MMO Catalyst. The reactions zones were cooled using a molten salt bath.

The reaction system further included an inter-condenser between the first and second reaction zones capable of cooling the effluent stream of the first reaction zone for the purpose of separating at least a portion of the oxidation product (acrylic acid) from the effluent stream prior to being fed to the second reaction zone. The inter-condenser was a typical shell-and-tube heat exchanger familiar to persons having ordinary skill in the art.

For all of the following Examples, reactant starting materials to the first reaction zone comprising 10 vol % propane, 9 vol % water (steam), 17 vol % oxygen, with the remainder being nitrogen, were fed to the two-stage reaction process. A residence time of 1.5 seconds was maintained for the reactants in both reaction zones (stages). The temperatures of both the first and second reaction zone were maintained between 340° C. and 380° C. and they were operated at atmospheric pressure. No recycle was employed for any of the Examples. In each Example, the compositions of the effluent streams of the first and second reaction zones were analyzed using a gas chromatograph (for gas phase effluent) and a liquid chromatograph (for liquid phase effluent).

COMPARATIVE EXAMPLE 1

Unsupported MMO Catalyst, No Interstage Condensation or Staged Oxygen

Each of the reaction zones was packed with the same volume of the above-described unsupported MMO Catalyst. No separation of the oxidation product from the effluent stream of the first reaction zone was performed. Rather, the entire effluent stream from the first reaction zone was fed into the second reaction zone with additional oxygen, in the form of molecular oxygen. A second effluent stream exited the second reaction zone and contained, among other things, acrylic acid (AA) and unreacted propane. The compositions of the effluent streams of the first and second reaction zones were analyzed and the results of the compositional analysis and calculations for the effluent streams are presented in Table 3 below, in terms of feed conversion and AA yield attributable to each reaction zone.

TABLE 3

| Reaction Zone (Stage) | Salt Bath Temperature (° C.) | Reactor Peak Temperature (° C.) | Cumulative Propane Conversion (%) | Acrylic Acid Selectivity, each stage (%) | Cumulative Acrylic Acid Yield (%) |
|---|---|---|---|---|---|
| First | 351 | 379 | 51.1 | 75.6 | 38.7 |
| Second | 352 | 364 | 63.1 | 80.2 | 50.6 |

COMPARATIVE EXAMPLE 2

Unsupported MMO Catalyst, with Interstage Condensation and Staged Oxygen

Each of the reaction zones is packed with the same volume of the above-described unsupported MMO Catalyst as used for Comparative Example 1. A portion of the oxidation product (AA) is separated from the effluent stream of the first reaction zone using the inter-condenser operating with chilled water at a temperature of 4° C. More particularly, the inter-condenser is expected to remove greater than 95 vol % of the AA formed in the first stage from the first stage effluent stream, to form an intermediate product stream containing primarily AA, as well as various other by-products, including, but not limited to, water and acetic acid.

The remaining portion of the effluent stream will form an intermediate feed stream which is fed into the second reaction zone with additional oxygen, in the form of molecular oxygen, in an amount such that the feed stream to the second reaction zone is non-flammable. A second effluent stream exits the second reaction zone and contains, among other things, acrylic acid (AA) and unreacted propane. The compositions of the effluent streams of the first and second reaction zones are analyzed and the expected results of the compositional analysis and calculations for the intermediate product stream and the effluent streams are presented in Table 4 below in terms of feed conversion and AA yield attributable to each reaction zone.

TABLE 4

| Reaction Zone (Stage) | Salt Bath Temperature (° C.) | Reactor Peak Temperature (° C.) | Cumulative Propane Conversion (%) | Acrylic Acid Selectivity, each stage (%) | Cumulative Acrylic Acid Yield (%) |
|---|---|---|---|---|---|
| First | 351 | 379 | 49.9 | 77.6 | 38.7 |
| Second | 361 | 371 | 74.7 | 81.2 | 60.7 |

EXAMPLE 3

MMO Catalyst Supported on Cordierite Monoliths, with Interstage Condensation and Staged Oxygen Each of the reaction zones is packed with the same volume of the cordierite-supported MMO Catalyst as the volume of unsupported MMO Catalyst used for Comparative Examples 1 and 2. A portion of the oxidation product (AA) is separated from the effluent stream of the first reaction zone using the inter-condenser operating with chilled water at a temperature of 4° C. More particularly, the inter-condenser is expected to remove greater than 95 vol % of the AA formed in the first stage from the first stage effluent stream to form an intermediate product stream containing primarily AA, as well as various other by-products, including, but not limited to, water and acetic acid.

The remaining portion of the effluent stream forms an intermediate feed stream which is fed into the second reaction zone with additional oxygen, in the form of molecular oxygen, in an amount such that the feed stream to the second reaction zone is non-flammable. A second effluent stream exits the second reaction zone and contains, among other things, acrylic acid (AA) and unreacted propane. The compositions of the effluent streams of the first and second reaction zones are analyzed and the expected results of the compositional analysis and calculations for the intermediate product stream and the effluent streams are presented in Table 5 below in terms of feed conversion and AA yield attributable to each reaction zone.

TABLE 5

| Reaction Zone (Stage) | Salt Bath Temperature (° C.) | Reactor Peak Temperature (° C.) | Cumulative Propane Conversion (%) | Acrylic Acid Selectivity, each stage (%) | Cumulative Acrylic Acid Yield (%) |
|---|---|---|---|---|---|
| First | 351 | 379 | 51.5 | 73.5 | 37.9 |
| Second | 361 | 371 | 71.7 | 79.2 | 56.8 |

From the foregoing Comparative Examples 1 and 2, it can be seen that the process of the present invention, including oxidation of propane in the presence of an unsupported Mo—V-based catalyst, as well as the steps of separating at least a portion of the oxidation product from interstage effluent streams and adding additional oxygen to the remaining portion prior feeding it to subsequent reaction zones, is expected to result in higher feed conversion and higher product yield. Furthermore, from the foregoing Comparative Example 2 and Example 3, it can be seen that the replacement of the unsupported Mo—V-based catalyst with the same catalyst composition supported on a wash-coated monolith, is expected to result in only slightly lower catalytic performance even though the mass of active Mo—V-based catalyst is reduced by more than half.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

What is claimed is:

1. A process for producing acrylic acid by vapor phase oxidation reaction of propane, propene, and mixtures thereof, using a reaction system having at least two reaction zones arranged in series with one another and at least one catalyst capable of catalyzing the vapor phase oxidation reaction disposed in each of the at least two reaction zones, wherein at least one intermediate effluent stream exits a preceding one of the at least two reaction zones and is at least partially fed to a subsequent one of the at least two reaction zones, and wherein said at least one catalyst comprises a three dimensional support and a mixed metal oxide having the empirical formula:

$$Mo_aV_bN_cX_dO_e$$

wherein N is at least one element selected from the group consisting of Te and Se; X is at least one element selected from the group consisting of Nb, Ta, Ti, Al, Zr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and wherein a, b, c, d and e are, respectively, the atomic ratios of molybdenum, vanadium, N, X and oxygen, and when a=1, b=0.01 to 1.0, c=0.01 to 1.0, d=0.01 to 1.0, and e is dependent on the oxidation state of the other elements, said process comprising the steps of:

separating the at least one intermediate effluent stream by cooling the at least one intermediate effluent stream such that at least a portion of the acrylic acid condenses out of the at least one intermediate effluent stream to form at least an intermediate product stream comprising acrylic acid and an intermediate feed stream comprising starting materials selected from the group consisting of unreacted propane, unreacted propene, and mixtures thereof;

feeding the intermediate feed stream to the subsequent reaction zone; and feeding an oxygen-containing gas to the subsequent reaction zone.

2. The process according to claim 1, wherein said three dimensional support comprises a ceramic form selected from the group consisting of open or closed cell ceramic foams and ceramic monoliths.

3. The process according to claim 2, wherein said ceramic form comprises at least one material selected from the group consisting of: cordierite, alumina, zirconia, silica, aluminosilicate zeolites, phosphosilicate zeolites PSZ, and other zeolites.

4. The process according to claim 1, wherein the element N in said at least one catalyst comprises Te, and the element X comprises Nb.

5. The process according to claim 1, further comprising the step of feeding oxygen-containing gas to a first one of the at least two reaction zones.

6. The process according to claim 1, wherein said separating step is performed using an absorber.

7. The process according to claim 1, wherein at least two of the at least two reaction zones are contained within a single reactor vessel.

8. The process according to claim 1, further comprising the step of providing the propane, propene, or mixture thereof, to each of the at least two reaction zones in an amount ranging from 7 vol % to 25 vol %, based on the total volume of starting materials being fed.

9. The process according to claim 1, wherein each of the at least two reaction zones is maintained at a temperature in the range of from 200° C. to 700° C.

10. The process according to claim 1, wherein the starting materials have a contact time with the at least one catalyst In each of the at least two reaction zones in the range of from 0.1 to 10 seconds.

* * * * *